United States Patent [19]

Sinkula

[11] 4,049,700

[45] Sept. 20, 1977

[54] IBUPROFEN P-HYDROXYPHENYLUREA ESTER

[75] Inventor: Anthony A. Sinkula, Kalamazoo, Mich.

[73] Assignee: The Upjohn Company, Kalamazoo, Mich.

[21] Appl. No.: 696,947

[22] Filed: June 17, 1976

[51] Int. Cl.² .......................................... C07C 127/19
[52] U.S. Cl. .................................... 560/105; 424/308
[58] Field of Search ......................................... 260/477

[56] References Cited

U.S. PATENT DOCUMENTS 3,931,285  1/1976  Morozowich ................... 260/468 D

*Primary Examiner*—Jane S. Myers
*Attorney, Agent, or Firm*—Hans L. Berneis

[57] ABSTRACT

Ibuprofen p-hydroxyphenylurea ester having the formula II:

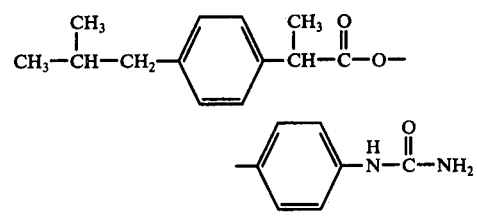

was prepared from the free acid, ibuprofen [±2-(p-isobutylphenyl)propionic acid](I).

The ester II above has the anti-inflammatory activity of the free acid, but in contradistinction to it, it has a pleasant taste, suitable for oral administration such as uncoated tablets, suspensions or syrups, for the treatment of inflammatory conditions, particularly arthritis.

1 Claim, No Drawings

IBUPROFEN P-HYDROXYPHENYLUREA ESTER

BACKGROUND OF THE INVENTION

Ibuprofen (Motrin®) is one of the more recent commonly prescribed, non-steroidal drugs used in the treatment of arthritis. It is used in dosages of 300–400 mg. tablets up to 8 per day. The taste of this propionic acid derivative is extremely repulsive, which makes it necessary to coat the tablet or to capsulate the product. It is very difficult to veil this taste by other added flavors in syrup formulations. Therefore, the practical, effective dosage are coated tablets or capsules which in view of the dosage requirement are of large size and thus present a difficulty of swallowing, particularly for children or older people.

It has now been found that the novel p-hydroxyphenylurea ester of ibuprofen II provides an effective form of the active parent compound, Compound II, is nearly tasteless and thus permits the production of liquid forms for administration specifically suitable for the pediatric or geriatric patient.

The ethyl ester of ibuprofen is named in U.S. Pat. No. 3,228,831. This ester is an oil and its taste qualities are not markedly different from the parent ibuprofen.

FIELD OF THE INVENTION

This invention is directed to nearly tasteless ibuprofen p-hydroxyphenylurea ester and the process of production thereof.

The novel compound and the process of production thereof can be illustratively represented as follows:

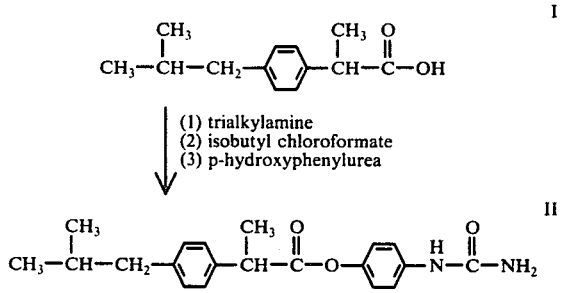

The invention includes besides the novel compound II, the process to make compound II.

The compound I, ibuprofen, can be alternatively named p-(iso-butyl)hydratropic [see hydratropic acid, Dictionary of Organic Compounds, Heilbron, Vol. II, p. 699, New York, Oxford Press, 1953]or α-methyl-α-(p-isobutylphenyl)acetic acid. Consequently the compound herein preferably named as ibuprofen p-hydroxyphenyl ester can be named by any of the alternative names for ibuprofen.

The process of this invention comprises: treating ibuprofen I dissolved in an inert organic solvent with a trialkylamine in which the alkyl group is of 1 to 4 carbon atoms, inclusive, between $-50°$ to $0°$ C.; treating the mixture with isobutylchloroformate and subsequently with (p-hydroxyphenyl)urea dissolved in an inert organic base at a temperature of $-10°$ to $40°$ C.

PREFERRED EMBODIMENT OF THE INVENTION

The new ester II, ibuprofen p-hydroxyphenylurea ester, was tested in the hind paw test for anti-inflammatory efficacy. It was found that the product had a potency of 1.7 × aspirin which is approximately the same as ibuprofen itself. On the other hand in a taste panel, where 9 is the highest score (excellent taste) and zero is the lowest, ibuprofen (I) has a score of 3, while the p-hydroxyphenylurea ester has a score of 7.

The ester II can thus be administered orally in the form of pills, tablets, dragees, and the like containing specific dosages, 100–500 mg., of the active material. Similarly, the ester II may be administered in liquid forms such as solutions, suspensions, syrups, emulsions, with flavors and common solvents or diluents, containing precise dosages per liquid unit dosage such as from 75 to 500 mg. per teaspoon (5 ml.) or per tablespoon (15 ml.).

In carrying out the process of this invention, the starting compound ibuprofen (I) is dissolved in an inert organic solvent, e.g. ether, such as diethyl ether, dipropylether, dioxane, tetrahydrofuran, ketones such as acetone, diethyl ketone, pentanones, hexanone, cyclohexanone or the like and the solution is first admixed with a trialkyl amine e.g. triethyl-, tripropyl-, methyldiethylamine or the like at temperatures between $-50°$ to $0°$ C., conveniently at room temperature. To this reaction after cooling to between $-30°$ to $0°$ C, isobutylchloroformate is added, and shortly thereafter the p-hydroxyphenylurea at a temperature of $-10°$ to $40°$ C. The mixture is allowed to react between 10 to 120 minutes, longer times can be used, however, no advantages are obtained thereby. In the preferred embodiment of this invention the three reagents used, that is a trialkylamine, isobutyl chloroformate and p-hydroxyphenylurea are used in a ratio of 1 to 1.5 mole eqivalent to 1 mole equivalent of ibuprofen. Larger ratios are operative, but are not advantageous.

After the reaction is terminated the reaction mixture is acidified to a pH of 1.5–3.0 and the product II is recovered by extraction with an inert organic solvent in conventional manner.

EXAMPLE 1

Ibuprofen p-hydroxyphenylurea ester

Ibuprofen, p-isobutylhydratropic acid, (8 g., 3.8 × $10^{-2}$ mole) was dissolved in 10 ml. of anhydrous acetone. To this solution was added 3.92 g. (3.8 × $10^{-2}$ mole) of triethylamine. This was cooled to $-20°$ C. under nitrogen and thereto was added 5.30 g. (3.8 × $10^{-2}$ mole) of isobutyl chloroformate. The resulting solution was allowed to warm to between $-5°$ C to $0°$ C. and thereupon 5.90 g. (3.8 × $10^{-2}$ mole) of p-hydroxyphenylurea in 50 ml. of pyridine was added under continuous stirring. After 1 hour the pH was adjusted to 2 by adding a sufficient amount of aqueous dilute 1.0N hydrochloric acid. The acidified solution was then extracted with ether, the ether layer dried over anhydrous magnesium sulfate and the solvent removed in vacuo. The resulting crystals were recrystallized from methanol-water providing ≅3 g. of ibuprofen p-hydroxyphenylurea ester of melting point 155°–159° C.

Anal. calcd. for $C_{20}H_{24}N_2O_3$: C, 70.56; H, 7.11; N, 8.23. Found: C, 70.25; H, 7.17; N, 8.11.

EXAMPLE 2

Pediatric Suspension

A pediatric suspension containing 82 mg. of the ester which is equivalent to 50 mg. of ibuprofen per teaspoon (5 ml.) is made from the following types and amounts of ingredients

| Ibuprofen p-hydroxyphenylurea ester | 16.4 | gm. |
| --- | --- | --- |
| Tragacanth | 10.0 | gm. |
| Benzoic acid | 2.0 | gm. |
| Sodium saccharin | 1.0 | gm. |
| Glycerin | 10.0 | ml. |
| Peppermint oil | 0.75 | ml. |
| Purified water, q.s. | 1000 | ml. |

The ibuprofen p-hydroxyphenylurea is mixed with 500 ml. of the water. The tragacanth, saccharin and glycerin are triturated and added to the water. The benzoic acid and peppermint oil are added to the mixture in a small amount of water. Purified water is added to volume. One teaspoon of this suspension is administered to children 1-4 times a day.

EXAMPLE 3

Suspension

| Ibuprofen p-hydroxyphenylurea ester | 131.2 | gm. |
| --- | --- | --- |
| Microcrystalline cellulose | 12.0 | gm. |
| Sodium carboxymethylcellulose | 10.0 | gm. |
| Cherry flavor | 0.5 | gm. |
| Purified water, q.s. | 1000 | ml. |

Each teaspoonful (5 ml.) contains 656 mg. of the ester which is equivalent to 400 mg. of ibuprofen. The microcrystalline cellulose is dispensed in the water with a high-shear mixer. The sodium carboxymethylcellulose is added and dissolved by means of a high-shear mixer. The ester and flavor are added and mixed and the whole homogenized. This is administered to adults at a dose of one teaspoonful 1-4 times a day.

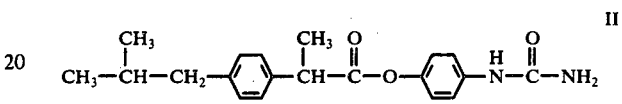

I claim:

1. Ibuprofen p-hydroxyphenyurea ester having the formula II: